US010973604B2

(12) United States Patent
Distler et al.

(10) Patent No.: US 10,973,604 B2
(45) Date of Patent: Apr. 13, 2021

(54) METHOD TO CALIBRATE A LIGHT UNIT, STORAGE MEDIUM, APERTURE PLATE AND MEDICAL IMAGING APPARATUS

(71) Applicant: Siemens Healthcare GmbH, Erlangen (DE)

(72) Inventors: Ferdinand Distler, Erlangen (DE); Matthias Baer-Beck, Erlangen (DE); Jochen Ostermaier, Erlangen (DE); Volker That, Forchheim (DE); Frauke Eenboom, Forchheim (DE); Kay Uwe Seemann, Emskirchen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/935,375

(22) Filed: Jul. 22, 2020

(65) Prior Publication Data

US 2021/0030512 A1    Feb. 4, 2021

(30) Foreign Application Priority Data

Aug. 1, 2019 (EP) ..................... 19189579

(51) Int. Cl.
*A61B 90/00* (2016.01)
*A61B 5/00* (2006.01)
(Continued)

(52) U.S. Cl.
CPC ............ *A61B 90/39* (2016.02); *A61B 5/0073* (2013.01); *A61B 6/03* (2013.01); *A61B 6/582* (2013.01);
(Continued)

(58) Field of Classification Search
CPC ....... A61B 90/39; A61B 5/0073; A61B 6/582; A61B 6/03; A61B 90/30; A61B 2090/3937; G03B 21/2033
See application file for complete search history.

(56) References Cited

U.S. PATENT DOCUMENTS

| 2009/0234370 A1 | 9/2009 | Haras |
| 2012/0220863 A1 | 8/2012 | Hannemann |
| 2013/0188782 A1 | 7/2013 | Hannemann |

FOREIGN PATENT DOCUMENTS

| DE | 2945251 A1 | 5/1981 |
| DE | 102013010515 A1 | 12/2014 |

OTHER PUBLICATIONS

Extended European Search Report for Application No. /Patent No. 19189579.6-1122 dated Jan. 17, 2020.

*Primary Examiner* — Sanjay Cattungal
(74) *Attorney, Agent, or Firm* — Harness, Dickey & Pierce, P.L.C.

(57) ABSTRACT

A method is used to calibrate a light unit, including at least one light source, the light unit being part of a medical imaging apparatus. In an embodiment, the method includes positioning a calibration phantom at a calibration position, in particular a first calibration position; arranging the light source so that its beam illuminates the photodetector at least partially; starting or continuing the recording of light intensities using the photodetector; modulating the signal of the light source at least once; rotating the light beam around a given rotation axis while recording the rotational position; synchronizing the time values of the rotational position of the light beam and the acquired signal intensities using the modulation of the light signal; and mapping the rotational position, in particular the rotation angle, of the light beam to a spatial position using the light intensities recorded by the photodetector.

19 Claims, 5 Drawing Sheets

(51) Int. Cl.
*A61B 6/00* (2006.01)
*A61B 90/30* (2016.01)
*A61B 6/03* (2006.01)
*G03B 21/20* (2006.01)

(52) U.S. Cl.
CPC ...... *A61B 90/30* (2016.02); *A61B 2090/3937* (2016.02); *G03B 21/2033* (2013.01)

METHOD TO CALIBRATE A LIGHT UNIT, STORAGE MEDIUM, APERTURE PLATE AND MEDICAL IMAGING APPARATUS

PRIORITY STATEMENT

The present application hereby claims priority under 35 U.S.C. § 119 to European patent application number EP 19189579.6 filed Aug. 1, 2019, the entire contents of which are hereby incorporated herein by reference.

FIELD

Embodiments of the invention generally relate to a method to calibrate a light unit, the light unit being part of a medical imaging apparatus.

BACKGROUND

It is known to use medical imaging apparatus to guide interventions. This is called interventional radiology.

Additionally, it is known to use laser guidance to support medical personnel e.g. by positioning a needle at a certain position and angle into the body of a patient.

Both techniques may be combined using a laser unit or generally a light unit positioned on a medical imaging system.

This light unit is used to mark the desired position and angle on the body surface of the patient.

From US 2009/0234370 A1, a computed tomography apparatus is known that has two fan lasers with which a guideline for a medical instrument can be marked. The fan lasers are arranged so as to be adjustable on the gantry of the computed tomography apparatus in order to be able to identify different planes in space or to mark different guidelines in space.

The adjustment of the laser beams is organized by markers positioned at predetermined positions.

US 2012/0220863 A1 shows a computed tomography apparatus again having two fan lasers. The fan-shaped light beams are reflected at mirrors, the mirrors being rotatable around a mirror rotation axis. This extends the positions where planes in space can be marked.

To calibrate the light units, it is also known to use calibration phantoms. These phantoms contain photodiodes to detect the projected light beams. The calibration phantoms are usually pluggable and only connected during the calibration process.

To connect the data recorded by the calibration phantom and the light unit during the calibration process a synchronization of the timing of the devices is necessary. The absolute time is not necessary for calibration purposes. Only the past time after a starting time tO is needed to connect the data.

SUMMARY

The inventors have discovered that there is a need for a method to calibrate a light unit having at least one light source, the light source being part of a medical imaging apparatus. The method has to be executed automatically.

A method according to at least one embodiment of the invention, comprises:

a) providing a calibration phantom having at least one photodetector,
b) positioning the calibration phantom at a calibration position, in particular a first calibration position,
c) arranging the light source so that its beam illuminates the photodetector at least partially,
d) starting or continuing the recording of light intensities using the photodetector,
e) modulating the light signal of the light source at least once,
f) rotating the light beam around a given rotation axis while recording the rotational position,
g) synchronizing the time values of the rotational position of the light beam and the acquired signal intensities using the modulation of the light signal, and
h) mapping the rotational position, in particular the rotation angle, of the light beam to a spatial position using the light intensities recorded by the photodetector.

In accordance with another embodiment of the invention, a calibration phantom is disclosed the calibration phantom having a base unit with at least one photo detector, the calibration phantom having an aperture plate with at least one aperture placed above the photodetector, the area of the aperture being smaller than the area of the photo detector. The apertures define the measuring point of the photodetectors more precise.

In accordance with another embodiment of the invention, a medical imaging apparatus is disclosed comprising:

a data acquisition scanner,
a memory in which instructions are stored,
a computer having access to said memory and being configured to read said instructions from said memory. In at least one embodiment, the computer is configured to carry out at least one embodiment of the method described above.

In accordance with another embodiment of the invention, a non-transitory computer-readable data storage medium encoded with programming instructions is disclosed, the storage medium being loadable into a computer system of a medical imaging apparatus that includes a computer system having a memory, the programming instructions causing the computer system to carry out at least one embodiment of the method described above, when executed.

In accordance with another embodiment of the invention, a method to calibrate a light unit including at least one light source, the light unit being configured for use in a medical imaging apparatus, comprises:

positioning a calibration phantom, including at least one photodetector, at a calibration position;
arranging the at least one light source so that a light beam of the at least one light source at least partially illuminate the at least one photodetector;
starting or continuing recording of light intensities using the at least one photodetector;
modulating a light signal of the light beam of the at least one light source at least once to acquire signal intensities;
rotating the light beam around a rotation axis while recording a rotational position;
synchronizing time values of the rotational position of the light beam and the signal intensities acquired using modulation of the light signal; and
mapping the rotational position of the light beam to a spatial position using the light intensities recorded by the at least one photodetector.

In accordance with another embodiment of the invention, a method to calibrate a light unit including at least one light source, comprises:

positioning an aperture plate at a calibration position, the aperture plate including at least one aperture, an area of the at least one aperture being relatively smaller than an area of at least one photodetector;

arranging the at least one light source so that a light beam of the at least one light source at least partially illuminate the at least one photodetector;

starting or continuing recording of light intensities using the at least one photodetector;

modulating a light signal of the light beam of the at least one light source at least once to acquire signal intensities;

rotating the light beam around a rotation axis while recording a rotational position;

synchronizing time values of the rotational position of the light beam and the signal intensities acquired using modulation of the light signal; and mapping the rotational position of the light beam to a spatial position using the light intensities recorded by the at least one photodetector.

In accordance with another embodiment of the invention, a calibration phantom comprises:

a base unit including at least one photodetector; and an aperture plate, the aperture plate including at least one aperture placed above the at least one photodetector an area of the at least one aperture being relatively smaller than an area of the at least one photodetector.

In accordance with another embodiment of the invention, a non-transitory computer-readable data storage medium is encoded with programming instructions, the non-transitory computer-readable data storage medium being loadable into a computer system of a medical imaging apparatus including a data acquisition scanner, the programming instructions causing the computer system to carry out the method of claim 1 upon execution by the computer system.

In accordance with another embodiment of the invention, a medical imaging apparatus comprises:

a data acquisition scanner;

a memory, to store programming instructions;

a computer having access to the memory and being configured to read the programming instructions from the memory, to calibrate a light unit of the medical imaging apparatus including at least one light source, by at least:

positioning a calibration phantom, including at least one photodetector, at a calibration position;

arranging the at least one light source so that a light beam of the at least one light source at least partially illuminate the at least one photodetector;

starting or continuing recording of light intensities using the at least one photodetector;

modulating a light signal of the light beam of the at least one light source at least once to acquire signal intensities;

rotating the light beam around a rotation axis while recording a rotational position;

synchronizing time values of the rotational position of the light beam and the signal intensities acquired using modulation of the light signal; and mapping the rotational position of the light beam to a spatial position using the light intensities recorded by the at least one photodetector.

BRIEF DESCRIPTION OF THE DRAWINGS

Further details of embodiments of the invention are provided below.

Parts that correspond to one another are labeled with the same reference characters in all figures.

DETAILED DESCRIPTION OF THE EXAMPLE EMBODIMENTS

Figure 1:
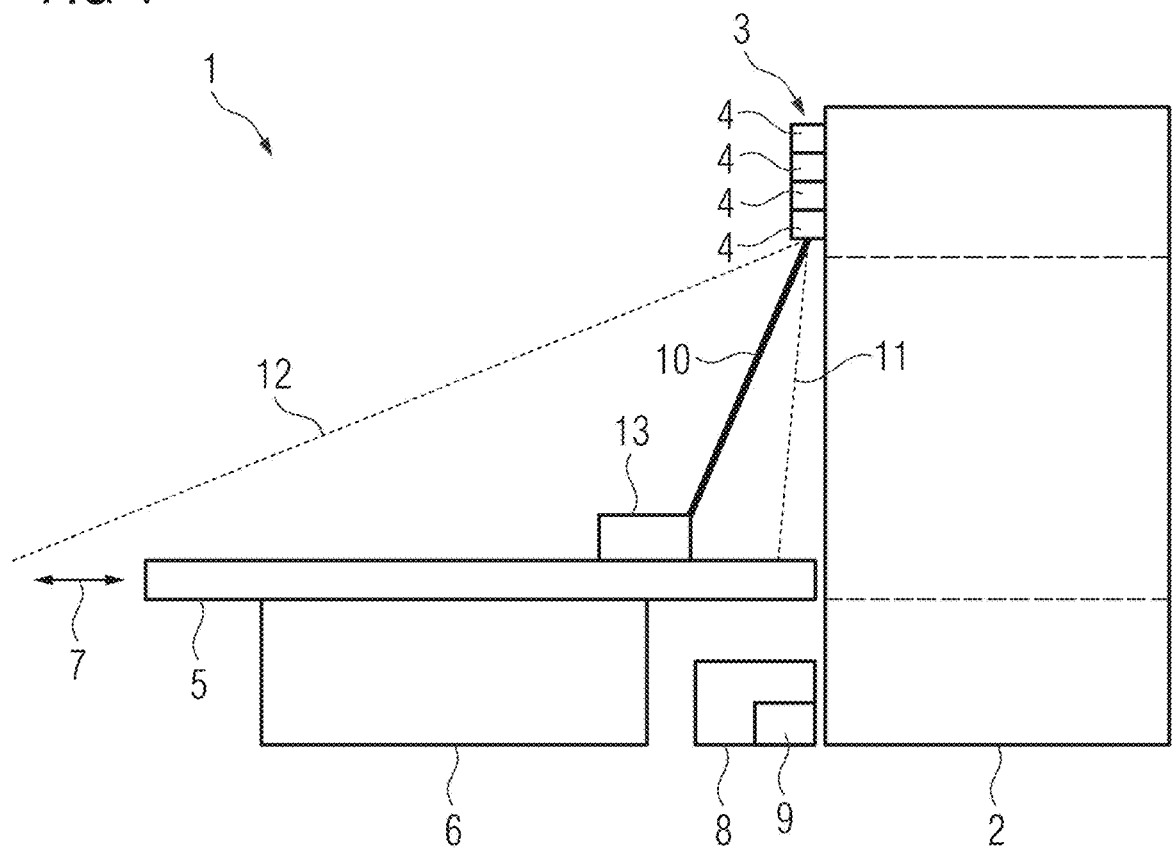
FIG. 1 shows an embodiment of a computed tomography apparatus.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central At least one processor (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central At least one processor (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer at least one processors into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

A method according to at least one embodiment of the invention, comprises:
i) providing a calibration phantom having at least one photodetector,
j) positioning the calibration phantom at a calibration position, in particular a first calibration position,
k) arranging the light source so that its beam illuminates the photodetector at least partially,
l) starting or continuing the recording of light intensities using the photodetector,
m) modulating the light signal of the light source at least once,
n) rotating the light beam around a given rotation axis while recording the rotational position,
o) synchronizing the time values of the rotational position of the light beam and the acquired signal intensities using the modulation of the light signal, and
p) mapping the rotational position, in particular the rotation angle, of the light beam to a spatial position using the light intensities recorded by the photodetector.

The calibration phantom of course has to be positioned at a place where the beam of the light source can illuminate the calibration phantom. The position may be exactly determined with regard to the position of the light source. Preferably the position has not to be determined exactly but only has to be in a certain area. Both alternatives will be discussed in detail later.

Then the light source is arranged in a way that its light beam illuminates the photo detector. This does not mean that personnel has to do it because an automatic procedure is preferred. But basically it could be done by hand.

After the light source has been positioned the recording of light intensities by the photo detector is started at the latest. It can be started before but not later.

The reason is that the detection of the light intensities is used for creating a time correlation between the light source and the photodetector and hence to synchronize them. This is realized by a modulation of the light signal of the light source. The modulation here is a modulation of the light intensity which can be controlled.

After the modulation of the light signal the light beam is rotated around a given rotation axis. This is necessary because the light beam does not perfectly fit to the area of the photo detector. Additionally, the light beam may have a certain shape. The recorded light intensities then help to identify the position of the center of the light beam.

The rotational position of the light beam at predetermined time points usually are recorded by the actuator of the light source together with the time point. The photodetector also records timing information together with the light intensities. Hence the rotation angles can be correlated to light intensities.

This basic method creates a correlation between the rotation angles of the light beam and the light intensities recorded by the photo detector. Using a time stamp by the application of at least one signal modulation results in a delay of less than 0.1 ms and a respective spatial resolution.

It has to be noted that a rotation of the light beam can be reached by a rotation of the light source and/or a rotation of a mirror mirroring the light beam. Then the rotational position of the light beam depends on the position of two actuators.

One of the benefits of the proposed method is that besides the calibration phantom no additional hardware is needed.

Preferably the calibration phantom is placed on a patient table of the medical imaging apparatus. Then the light source is calibrated with a phantom at a position where the guidance takes place. Additionally, the height of the position of the patient table is known and can be used for calibration purposes.

The position of the light source can be determined as it is known in the art. If an electric motor rotates the light source the incremental position of which can be recorded and is used as a form of the rotation angle. In the case of an additional mirror two incremental positions have to be considered. It is not necessary to calculate a concrete angle for the starting point. For a specific light source, it is sufficient to know that an incremental position of an electric motor correlates to a signal intensity at a given place. The incremental position in other words is a relative angle and this is sufficient. It has not necessarily to be made absolute with regard to the medical imaging apparatus.

Preferably the signal modulation is a signal variation in a predetermined manner. This predetermined signal modulation can be made known to the control unit of the photo detector and can set a time step when the modulation occurs. Otherwise the signal intensities can be recorded without searching for modulations immediately but in a central processing unit.

In a first embodiment, the signal modulation is a light signal turn off for a predetermined time period. This modulation can be easily identified in the recordings of the light intensity. The time period to be used depends on the temporal resolution of the photodetector.

Alternatively, the signal modulation is a turn on of the light signal. After the arrangement of the light beam to illuminate the photo detector, the light source may be switched off before the signal intensity recordings of the photodetector start. Then the signal modulation may be a turn on of the light.

Moreover, the signal intensity can be changed for a predetermined time to a predetermined value, e.g. to 50% either of the maximal power or 50% of the previous power for half a second.

Furthermore, the signal modulation can comprise several signal turn ons and offs or intensity changes.

Generally, the photo detector probably detects light originating from either the sun or an illumination system in the room of the medical imaging apparatus. Therefore, a threshold to exclude these light sources may be used.

Above it has been mentioned that the arrangement of the light source can be done automatically or by hand. An automatic arrangement can be realized using a central processor as follows:

The actuator of the light source moves the light source to one of the end positions of the rotational movement. A signal having reached the position is received by the processor. Then the calibration phantom is started. After that the light beam is rotated stepwise until the photodetector of the calibration phantom detects a signal intensity exceeding a predetermined threshold. This excess is interpreted as an illumination by the light source.

Hence the light beam is arranged to illuminate the photodetector by rotating the light beam from an initial angle position stepwise above the surface of the patient table and the calibration phantom. This initial angle position is preferably one of the end positions of the rotational movement.

After the application of the signal modulation in one embodiment the internal clock of the light source is set to 0. Additionally or alternatively, after the detection of the signal modulation the internal clock of the calibration phantom or the photodetector is set to 0. Then the recorded light intensities and the recorded rotational positions can be correlated directly. This can be done without a combined processor because the application and detection are independent from such a processor. The recorded time is the elapsed time after the signal modulation.

Alternatively, the application of the signal modulation is recorded to have a timestamp with regard to the rotational position. A timestamp for the recorded light intensities can be calculated any time after the recording. Then an alignment of the recorded time points has to be done afterwards.

There may occur a delay between the application and the detection of the signal modulation and the reset of the internal clock. The reset may be implemented at near hardware level, therefore the delay is extremely short. If it was disturbing anyhow, the delay may be determined retrospectively from the recorded diode signal. It can be then used to correct the recorded time values.

The delay can also be determined during the calibration procedure if there are two signal modulations with a defined time interval. If the second modulation is applied after the reset of the internal clock of the calibration phantom, the difference between the time recorded by the calibration phantom and the known delay is the delay looked for.

Preferably, a laser, in particular a fan laser, is used as light source. Laser light has a sufficient intensity to be used for guidance.

Advantageously, the light unit comprises at least two light sources. Using fan lasers intersecting fan-shaped beams are used for marking. Using more than one light source all steps described to calibrate one light source have to be repeated for every further light source.

A light source may comprise a mirror to mirror the light beam projected by the light source.

Preferably, the light unit includes four light sources. Then also every region of obese people can be marked without problems.

If the calibration phantom is positioned only at one place during the calibration procedure, the position of the calibration phantom relative to the light source has to be measured with great effort. To omit this measurement the calibration phantom preferably is positioned at at least two, preferably at three different positions and the above described procedure is executed at every position. Then a triangulation can be used to determine the position of the light source relative to the medical imaging apparatus as well as to the calibration phantom.

Note that also the number of light sources multiplies the number of measurements.

To use the triangulation only one condition has to be fulfilled: the distance between the first position and the second position as well as the distance between the second position and the third position have to be known exactly. The absolute position of the first position is not necessary. The differences in the positions are known without effort if the calibration phantom is positioned on a patient table. The patient table can be moved very precise by a control unit.

Using the automatic detection of illumination and triangulation the calibration procedure can be executed by a processor after the positioning of the calibration phantom automatically.

The photodetector advantageously is a photodiode. The calibration phantom may comprise multiple photodetectors, in particular photodiodes.

Preferably the light unit, the calibration phantom and the patient table or any other device supporting the calibration phantom are connected. They may be connected to a central processor which carries out the calibration.

In accordance with another embodiment of the invention a calibration phantom is disclosed the calibration phantom having a base unit with at least one photo detector, the calibration phantom having an aperture plate with at least one aperture placed above the photodetector, the area of the aperture being smaller than the area of the photo detector. The apertures define the measuring point of the photodetectors more precise.

Preferably, the number of apertures is the same as the number of photodetectors. Then every aperture covers one photo detector.

This calibration phantom plate is particularly used in the procedure described above.

Advantageously, the aperture plate is made of metal. Alternatively, it can be made of glass.

Preferably, the calibration phantom has several apertures, the apertures having the same area. The diameter of the area may be between 0.5 mm to 3 mm.

Alternatively to the aperture plate photodiodes with an active area like the area of an aperture can be used.

Furthermore and alternatively to the aperture plate light pipes can be used which guide the light to photodiodes.

The aperture plate may have markers to place it on the calibration phantom. The markers may help to position the apertures in the middle of the photo detectors.

In accordance with another embodiment of the invention a medical imaging apparatus is disclosed comprising:
 a data acquisition scanner,
 a memory in which instructions are stored, a computer having access to said memory and being configured to read said instructions from said memory. In at least one embodiment, the computer is configured to carry out at least one embodiment of the method described above.

Every of the embodiments described with regard to the method also can be realized in the medical imaging apparatus.

In accordance with another embodiment of the invention a non-transitory computer-readable data storage medium encoded with programming instructions is disclosed, the storage medium being loadable into a computer system of a medical imaging apparatus that comprises a computer system having a memory, the programming instructions causing the computer system to carry out at least noe embodiment of the method described above, when executed.

Every of the embodiments described with regard to the method also can be realized in the data storage medium.

Preferably, the medical imaging apparatus is realized as computed tomography apparatus. The medical imaging apparatus advantageously has a movable patient table.

FIG. 1 shows a medical imaging apparatus 1 which is a computed tomography apparatus. Further embodiments of the medical imaging apparatus could be a magnetic resonance apparatus, an X-Ray apparatus, a PET apparatus, and so on. The medical imaging apparatus 1 has a gantry 2 and a laser unit 3 with four laser projectors 4 distributed around the front of the medical imaging apparatus 1.

A patient table 5 is seated on a base 6. The patient table can be moved axially along the direction of arrow 7.

A control computer 8 controls the operation of the medical imaging apparatus 1, in particular of the gantry 2, the laser unit 3 and the patient table 5.

The medical imaging apparatus 1 also has a non-transitory data storage medium 9 as part of the control computer 8 or independent thereof, on which computer code for carrying out calibration measurements is stored.

A fan-shaped beam 10 radiated by one of the lasers 4 is shown as an example. A first end position 11 and a second end position 12 of the rotation path are shown with dashed lines.

A calibration phantom 13 is positioned on the patient table 5. During calibration it may also be connected to computer 8.

Figure 2:
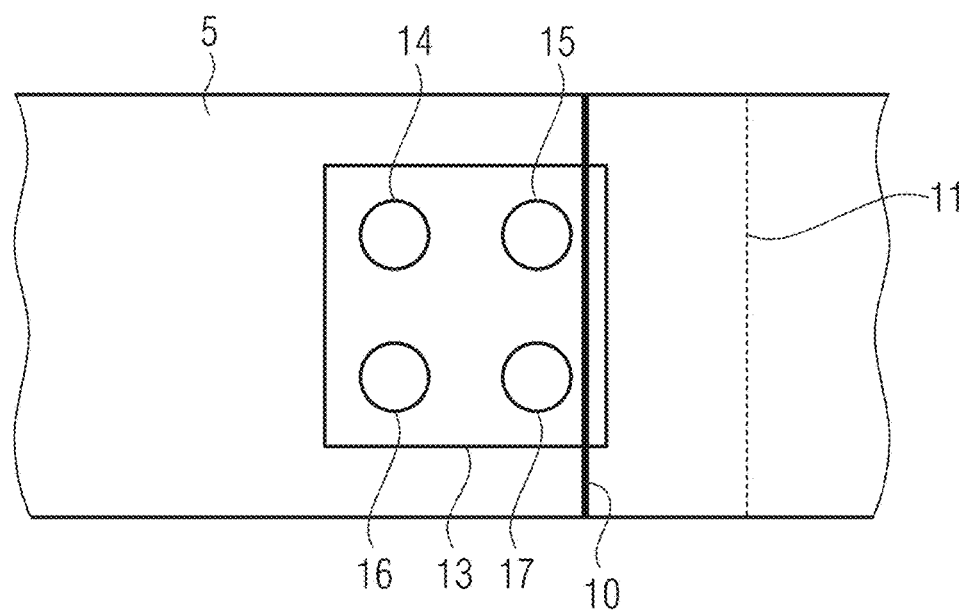
FIG. 2 shows a calibration phantom.

FIG. 2 shows the calibration phantom 13 in plan view. It has four photodiodes 14, 15, 16 and 17 as photodetectors. Also shown are the end position 11 and the fan-shaped beam 10 as shown in FIG. 1. End position 11 is outside the calibration phantom 13, but beam 10 illuminates photodiodes 15 and 17.

Figure 3:
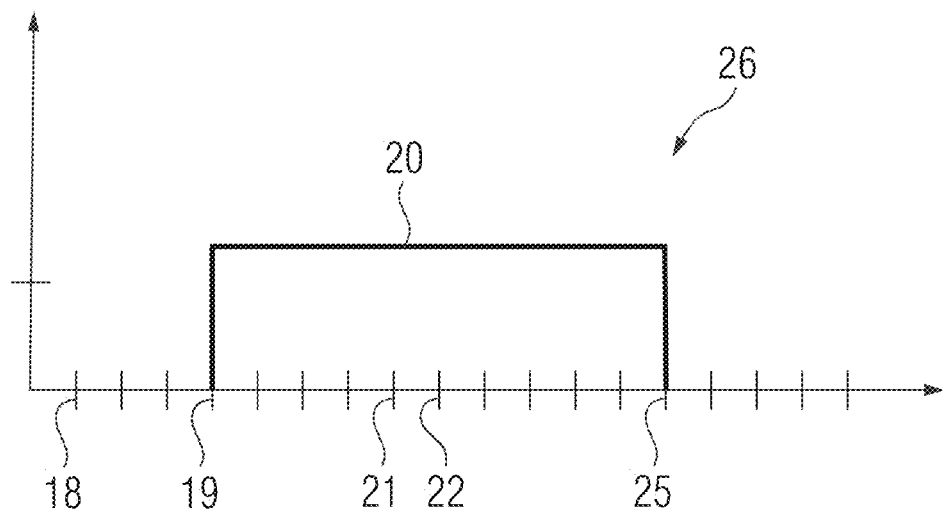
FIG. 3 shows a signal curve of a laser projector in a timing diagram of a signal modulation.
Figure 4:
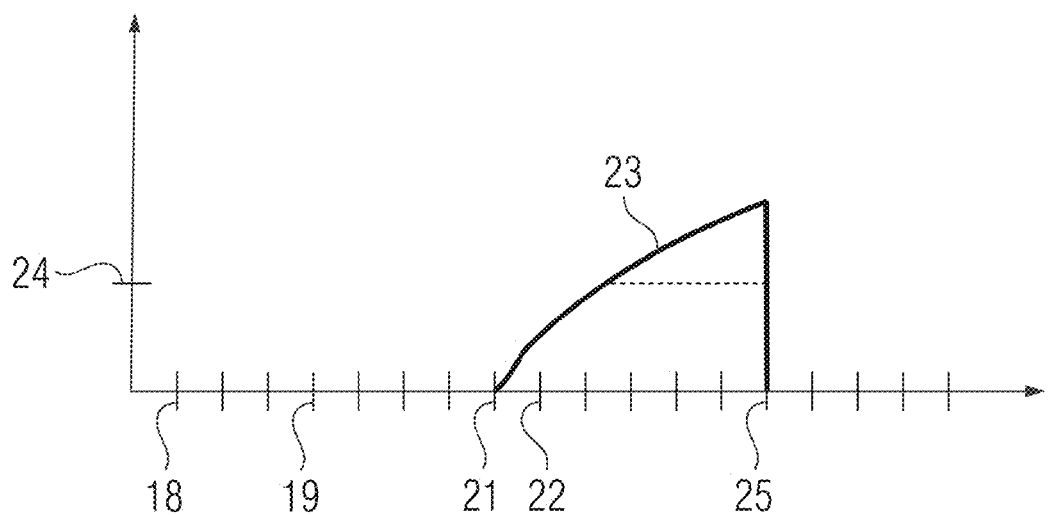
FIG. 4 shows a signal receive curve of a photodiode.

FIG. 3 shows a signal curve of a laser projector 4. FIG. 4 shows a corresponding signal receive curve of photodiode 15. At point 18 laser projector 4 has been rotated to the starting position, e.g. one of the rotational end points 11 or 12. At point 19 laser projector 4 is turned on. Here the emitted light shown by curve 20 is set to e.g. the maximal possible value. This is not a signal modulation because at this position laser projector 4 does not illuminate the calibration phantom 13.

Then beam 10 is rotated around its rotation axis: This rotation causes the beam 10 to move towards the calibration phantom 13. At point 21 beam 10 is on its way but still does not hit the calibration phantom 13. At point 22 beam 10 illuminates photo diode 15 slightly. The signal intensity detected by photo diode 15 and shown in curve 23 starts to increase. There curve 23 is still below threshold 24. When curve 23 reaches threshold 24 it is assumed that laser projector 4 illuminates photo diode 15. Then the control computer 8 turns at point 25 the laser projector 4 off, curve 20 drops to 0. This signal modulation 26 is detected by photodiode 15.

After the signal modulation took place the timer of the calibration phantom 13 and the laser projector 4 may be set to 0.

Then beam 10 is rotated further towards position 12. Thereby the rotational position of laser projector 4, e.g. by the incremental position of an electric motor rotating laser projector 4, and the signal intensity values detected by photo diodes 14 to 17 and the respective time points are recorded.

Without signal modulation 26 there was no timestamp to align the timers sufficiently, because known central computers 8 are not capable of doing so in a desired time period.

Figure 5:
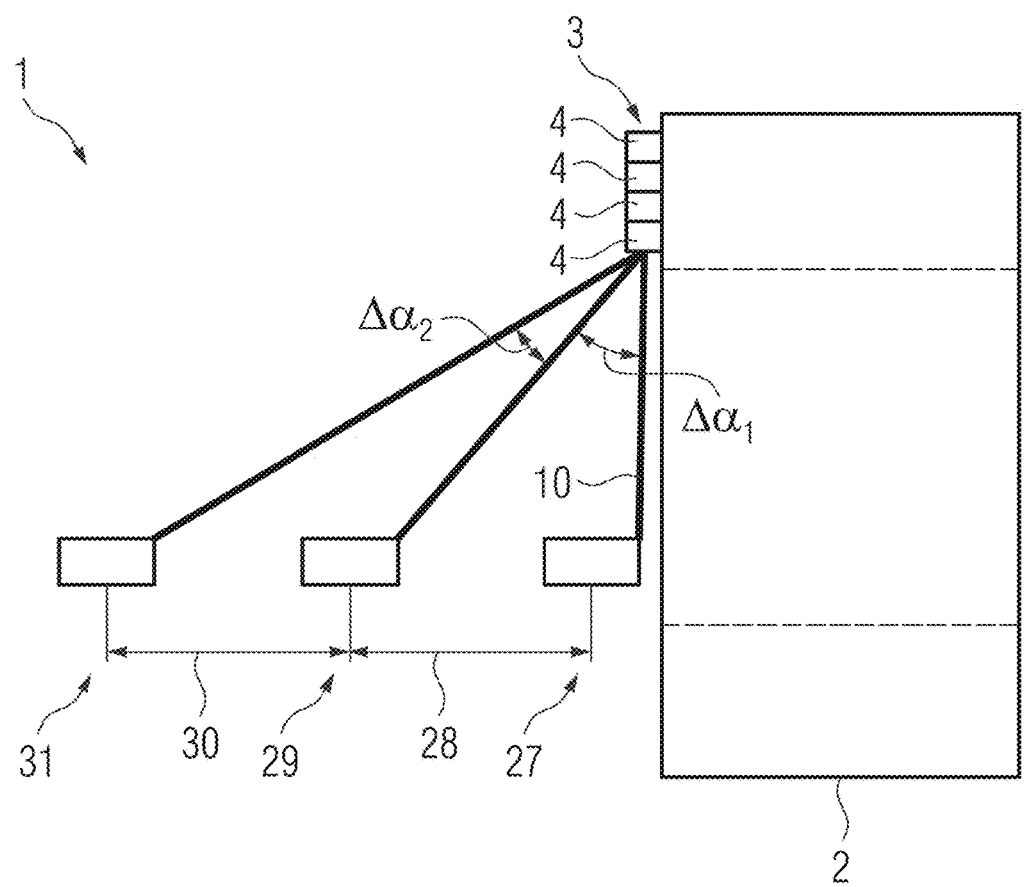
FIG. 5 shows a setup for calibration using triangulation.

FIG. 5 shows a setup for a calibration procedure which uses triangulation. There the calibration phantom is placed at a first position 27. There the measurements as described with regard to FIG. 3 and FIG. 4 are executed, one time for every laser projector 4. In the exemplary embodiment of FIG. 1 there were four laser projectors 4. Hence the measurement is done four times.

Then patient table 5 moves the calibration phantom 13 a predetermined distance 28 to the second position 29. Then the measurements are repeated again, here four times also at the second position 29. Distance 28 is exactly known and also the first difference angle $\Delta\alpha_1$. For a triangulation it is not necessary to know the angle of the first position 27, but only the difference between positions 27 and 29.

After that patient table 5 moves the calibration phantom 13 a predetermined distance 30 to a third position 31. Also predetermined distance 30 is exactly known. Executing the measurement as described above, a second angle difference $\Delta\alpha_2$ can be found.

It has to be noted that the predetermined distances 28 and 30 of course are identical for all four laser projectors 4, because the distances do not depend on the position of the laser projectors 4. The angle differences $\Delta\alpha_1$ and $\Delta\alpha_2$ will differ slightly due to the different position of laser projectors 4.

For every laser projector 4 three measurements have been made which are used to calibrate it.

Figure 6:
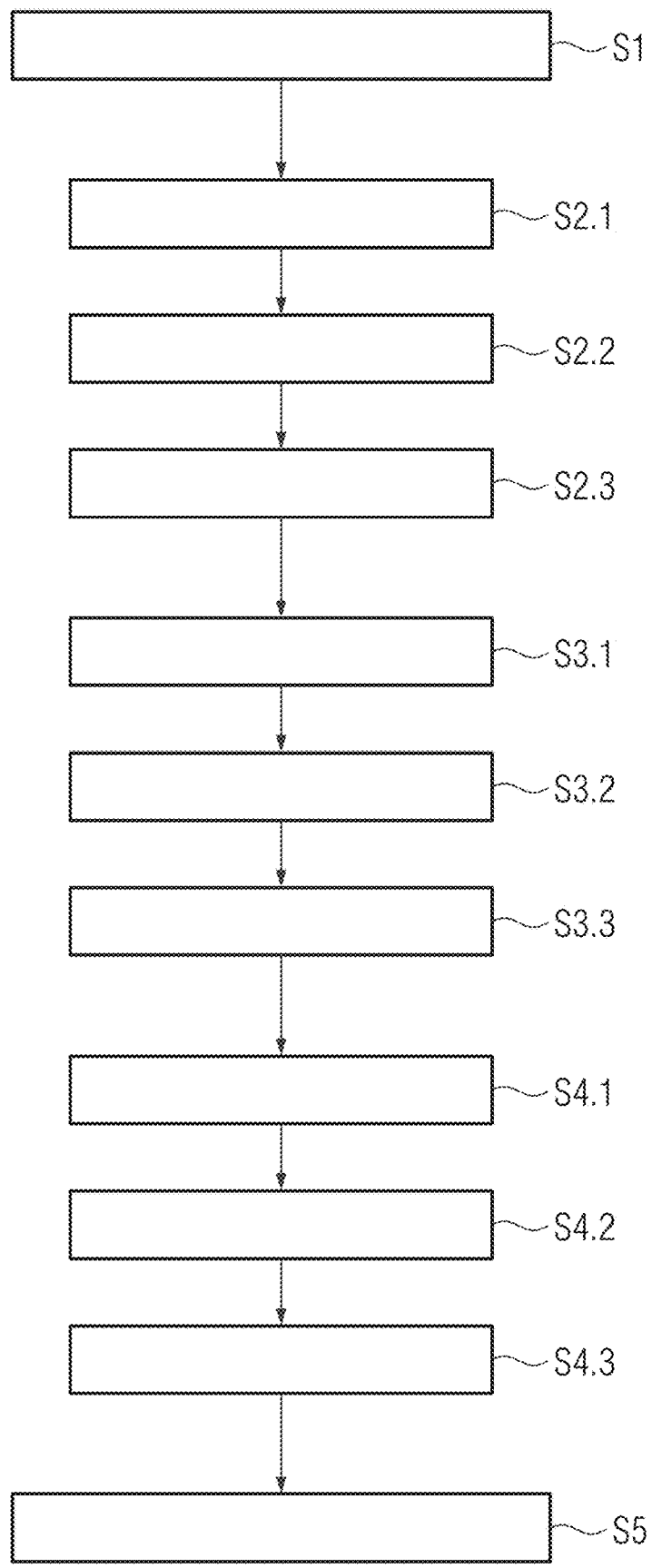
FIG. 6 shows a procedure diagram of calibrating a light unit.

FIG. 6 shows a procedure diagram of calibrating a light unit 3. In step S1 calibration phantom 13 is placed on the patient table 5. It must be put in a given area, e.g. at the distal end of the patient table 5. The distal end is that more distant to the gantry 2 than the other one.

Additionally, patient table 5 has been driven to a starting position from which it can be moved in a desired direction as described below. There the calibration phantom 13 is in the first position 27.

Position 27 is preferably some centimeters to some decimeters in front of the gantry 2.

Then the clocks of the laser unit 3 and the calibration phantom 13 are synchronized in step 2.1. This synchronization includes setting the internal clocks to 0.

Thereafter in step 2.2 the laser projectors 4 are arranged automatically to illuminate one of the photo diodes 14, 15, 16, or 17.

In step 2.3 the laser beams 10 of the laser projectors 4 are rotated as described one after another to have a first set of data. This set of data contains pairs of the rotational position and the signal intensity measured for that rotational position. The pairs are correlated over the point of time when they have been recorded. Every laser projector 4 has its own set of data.

After that patient table 5 drives the calibration phantom 13 to the second position 29 in step S3.1. The distance 28 between the first position 27 and the second position 29 is exactly known.

In steps S3.2 and S3.3 the arrangement and measurements are done in the same way as described to steps S2.2 and S2.3.

Then patient table 5 drives the calibration phantom 13 to the third position 31 as step S4.1. Also the distance 30 is exactly known.

In the following steps S4.2 and S4.3 the arrangement and measurements are done in the same way as described to steps S2.2 and S2.3.

Having collected all necessary data in step S5 angle differences $\Delta\alpha_1$ and $\Delta\alpha_2$ between the first position 27 and second position 29 or the second position 29 and the third position 31, respectively, can be calculated. Under consideration of distances 28 and 30 the calibration data are received.

Figure 7:
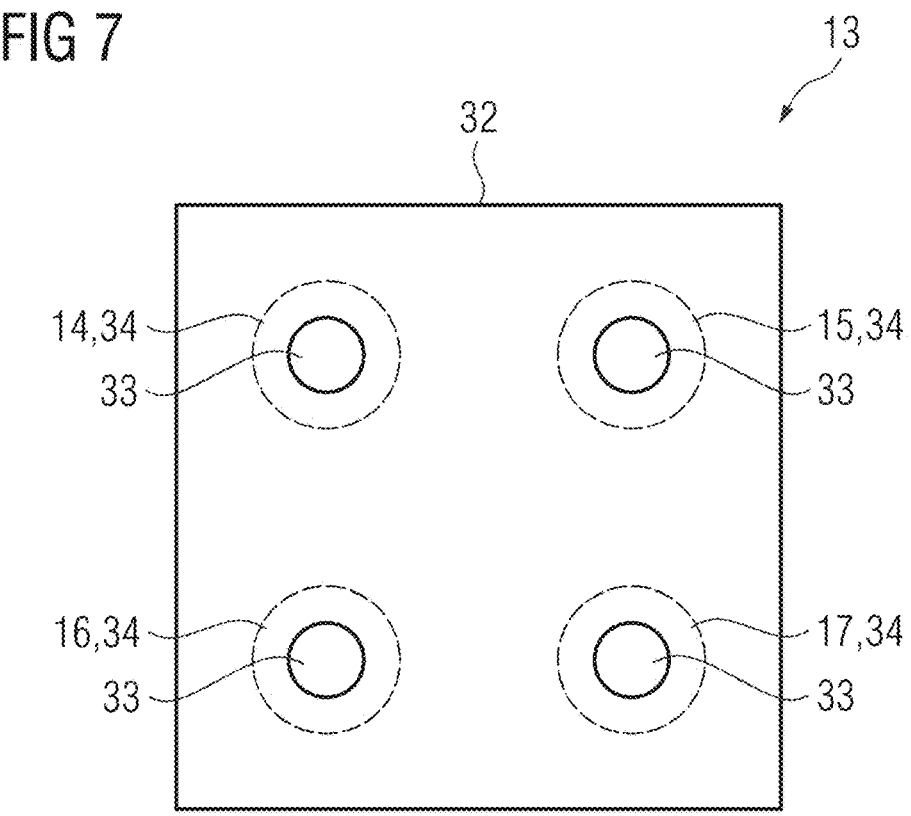
FIG. 7 shows a calibration phantom in a second embodiment in plan view.

FIG. 7 shows calibration phantom 13 in a second embodiment in plan view. The photo diodes 14, 15, 16 and 17 are covered partially by an aperture plate 32. The area of the apertures 33 is smaller than the area of the photo diodes which is indicated by dashed lines 34. Aperture plate 32 helps to define the spatial position of the fan-shaped beams more precise.

Figure 8:
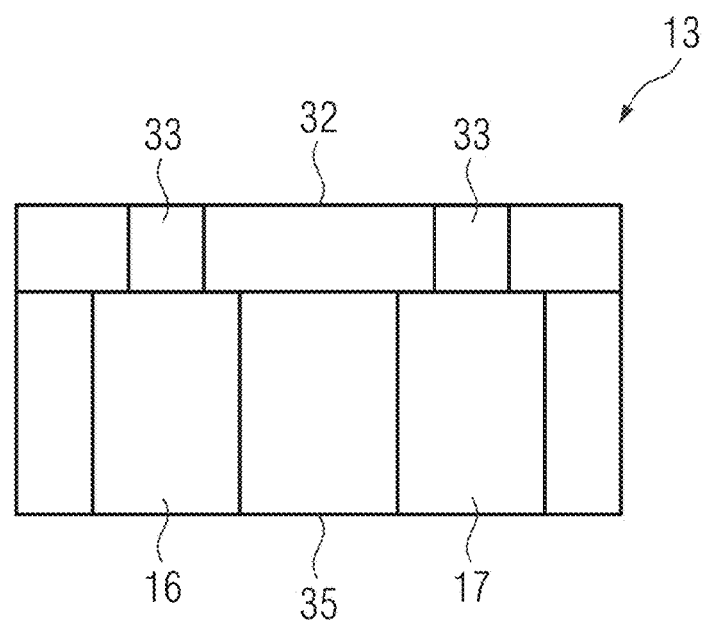
FIG. 8 shows a calibration phantom in a second embodiment in cross sectional view.

FIG. 8 shows the calibration phantom 13 according to FIG. 7 in a cross-sectional view. It can be seen that aperture plate 32 can be easily placed on basis 35 which has photo diodes 14, 15, 16 and 17. Aperture plate 32 is inexpensive and helps to improve the results of the calibration procedure independent of the procedure used for calibration.

Instead of the aperture plate 32 photodiodes having a smaller active area than the photodiodes 14, 15, 16 and 17 can be used.

A further alternative to aperture plate 32 is to use light pipes which guide the light to a photodiode.

Although the invention has been illustrated and described in greater detail with reference to the referred example embodiments, the invention is not restricted thereby. Other variations and combinations can be derived herefrom by the person skilled in the art without departing from the essential concept of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method to calibrate a light unit including at least one light source, the light unit being configured for use in a medical imaging apparatus, the comprising:
   positioning a calibration phantom, including at least one photodetector, at a calibration position;
   arranging the at least one light source so that a light beam of the at least one light source at least partially illuminate the at least one photodetector;
   starting or continuing recording of light intensities using the at least one photodetector;
   modulating a light signal of the light beam of the at least one light source at least once to acquire signal intensities;
   rotating the light beam around a rotation axis while recording a rotational position;
   synchronizing time values of the rotational position of the light beam and the signal intensities acquired using modulation of the light signal; and
   mapping the rotational position of the light beam to a spatial position using the light intensities recorded by the at least one photodetector.

2. The method of claim 1, wherein the modulating of the light signal includes a signal variation in a defined manner.

3. The method of claim 2, wherein the modulating of the light signal includes a light signal turn off for a time period.

4. The method of claim 2, wherein the modulating of the light signal includes a light signal turn on.

5. The method of claim 1, wherein the modulating of the light signal includes a light signal turn off for a time period.

6. The method of claim 1, wherein the modulating of the light signal includes a light signal turn on.

7. The method of claim 1, wherein the at least one light source is arranged to illuminate the at least one photodetector by rotating the light beam from an initial angle position stepwise above a surface of the calibration phantom.

8. The method of claim 7, wherein the at least partial illuminating of the at least one photodetector is set upon a threshold of signal intensity of the light beam being exceeded.

9. The method of claim 1, wherein at least one of an internal clock of the at least one light source and the calibration phantom, is set to 0 directly after the modulating of the light signal.

10. The method of claim 1, wherein a fan laser is used as the at least one light source.

11. The method claim 1, wherein the calibration phantom is positioned at three different positions and wherein a respective calibration measurement is executed at each position of the respective three different positions.

12. The method claim 1, wherein the method includes triangulation.

13. The method of claim 1, wherein the at least one light source of the light unit includes four light sources.

14. A non-transitory computer-readable data storage medium encoded with programming instructions, the non-transitory computer-readable data storage medium being loadable into a computer system of a medical imaging apparatus including a data acquisition scanner, the programming instructions causing the computer system to carry out the method of claim 1 upon execution by the computer system.

15. The method of claim 1, wherein the calibration position is a first calibration position.

16. The method of claim 1, wherein the mapping of the rotational position includes mapping of the rotation angle of the beam of the at least one light source to the spatial position using the light intensities recorded by the photodetector.

17. The method of claim 1, wherein an aperture plate is used including at least one aperture, an area of the at least one aperture being relatively smaller than an area of the at least one photodetector.

18. A method to calibrate a light unit including at least one light source, comprising:
   positioning an aperture plate at a calibration position, the aperture plate including at least one aperture, an area of the at least one aperture being relatively smaller than an area of at least one photodetector;
   arranging the at least one light source so that a light beam of the at least one light source at least partially illuminate the at least one photodetector;
   starting or continuing recording of light intensities using the at least one photodetector;

modulating a light signal of the light beam of the at least one light source at least once to acquire signal intensities;

rotating the light beam around a rotation axis while recording a rotational position;

synchronizing time values of the rotational position of the light beam and the signal intensities acquired using modulation of the light signal; and mapping the rotational position of the light beam to a spatial position using the light intensities recorded by the at least one photodetector.

19. A medical imaging apparatus, comprising:

a data acquisition scanner;

a memory, to store programming instructions;

a computer having access to the memory and being configured to read the programming instructions from the memory, to calibrate a light unit of the medical imaging apparatus including at least one light source, by at least:

positioning a calibration phantom, including at least one photodetector, at a calibration position;

arranging the at least one light source so that a light beam of the at least one light source at least partially illuminate the at least one photodetector;

starting or continuing recording of light intensities using the at least one photodetector;

modulating a light signal of the light beam of the at least one light source at least once to acquire signal intensities;

rotating the light beam around a rotation axis while recording a rotational position;

synchronizing time values of the rotational position of the light beam and the signal intensities acquired using modulation of the light signal; and mapping the rotational position of the light beam to a spatial position using the light intensities recorded by the at least one photodetector.

\* \* \* \* \*